(12) United States Patent
Huang

(10) Patent No.: US 9,068,747 B2
(45) Date of Patent: Jun. 30, 2015

(54) SYSTEMS, METHODS, AND COMPUTER PROGRAM PRODUCTS PROVIDING FLAME DETECTION

(71) Applicant: Safe-Fire, Inc., Irwindale, CA (US)

(72) Inventor: Zhigao Huang, Melbourne (AU)

(73) Assignee: SAFE-FIRE, INC., Irwindale, CA (US)

( * ) Notice: Subject to any disclaimer, the term of this patent is extended or adjusted under 35 U.S.C. 154(b) by 42 days.

(21) Appl. No.: 13/756,336

(22) Filed: Jan. 31, 2013

(65) Prior Publication Data

US 2014/0212824 A1   Jul. 31, 2014

(51) Int. Cl.
| | |
|---|---|
| F23N 5/08 | (2006.01) |
| F23N 5/24 | (2006.01) |
| G01J 5/00 | (2006.01) |
| G01N 21/72 | (2006.01) |

(52) U.S. Cl.
CPC ........... *F23N 5/082* (2013.01); *F23N 5/242* (2013.01); *F23N 2029/04* (2013.01); *F23N 2029/08* (2013.01); *F23N 2029/20* (2013.01); *G01J 5/0018* (2013.01); *G01N 21/72* (2013.01)

(58) Field of Classification Search
CPC ................ F23N 2029/00; F23D 2208/10
USPC ............................................................ 431/79
See application file for complete search history.

(56) References Cited

U.S. PATENT DOCUMENTS

| 5,625,342 | A | 4/1997 | Hall et al. | |
|---|---|---|---|---|
| 7,289,032 | B2 | 10/2007 | Seguin et al. | |
| 2005/0221243 | A1* | 10/2005 | Najewicz et al. | 431/18 |
| 2006/0199123 | A1* | 9/2006 | Seguin et al. | 431/75 |

FOREIGN PATENT DOCUMENTS

| WO | WO2006091616 | 8/2006 |
|---|---|---|
| WO | WO2006091617 | 8/2006 |

OTHER PUBLICATIONS

Technical Bulletin, "Uniflame—Unitized Flame Detector with Amplifier", Forney Corporation, Pub. No. 404005-08, Mar. 2005, 2 pgs.
"UniFlame® II Unitized Flame Detector", Forney Corporation, Pub. No. 404005-24, Apr. 2012, 2 pgs.
Technical Bulletin, "Digital profile Detector™", Forney Corporation, Pub. No. 404005-02, Nov. 2008, 2 pgs.
"D85 Unitized Flame Detector", Forney Corporation, Pub. No. 404005-26, Nov. 2012, 2 pgs.
"Type 85UVF/IRF Integrated Flame Scanner with Internal Flame Relay", Fireye, CU 114, Aug. 31, 2012, 30 pgs.

* cited by examiner

*Primary Examiner* — Kenneth Rinehart
*Assistant Examiner* — Jason Lau
(74) *Attorney, Agent, or Firm* — Haynes and Boone, LLP

(57) ABSTRACT

A system includes a flame detector with a photon detecting portion and a processing portion, the processing portion including a processor-based device programmed to provide the following functions: receiving input regarding a type of burner and a type of fuel, applying a flame detection configuration to the burner scanner according to the received input, and performing a flame detection process according to the flame detection configuration.

20 Claims, 3 Drawing Sheets

| | GAS | OIL | COAL |
|---|---|---|---|
| BURNER TYPE 1 | | | |
| BURNER TYPE 2 | | 530 | |
| BURNER TYPE 3 | | | |
| BURNER TYPE 4 | | | |
| ⋮ | ⋮ | ⋮ | ⋮ |
| BURNER TYPE N | | | |

Fig. 5

SYSTEMS, METHODS, AND COMPUTER PROGRAM PRODUCTS PROVIDING FLAME DETECTION

BACKGROUND

1. Technical Field

The present description relates, in general, to detecting a flame from a burner and, more specifically, to configuring a flame detector by identifying burner and fuel characteristics.

2. Related Art

Various applications use flame detectors (also called "flame scanners") to ensure proper operation of burners. For instance, blast furnaces, incinerators, industrial oil burners, power generators, and the like use burners, which are fed fuel and provide a flame within a chamber. In case of malfunction a burner may fail to produce a flame even though it is fed fuel, which is typically undesirable. Such applications may include flame detectors to identify whether a burner is providing a flame.

Most applications include multiple burners with one flame detector for each burner. A given flame detector is positioned so as to detect the light produced by its corresponding flame. However, in a system with multiple burners, a particular flame detector may have more than one flame within its line of sight. Thus, modern flame detectors attempt to identify a flame of interest by its features. Specifically, a given flame may be expected to have certain features, such as a flicker frequency that is affected by a frequency of fuel pulses at the burner, and a maximum and minimum intensity during its cycles. Also, a flame typically has a higher frequency closer to the burner nozzle and a lower frequency distal to the nozzle.

A given flame detector "looks" at a particular part of a flame that is expected to have a maximum intensity, minimum intensity, and frequency and compares received light to those flame parameters. Light that matches the parameters may be assumed to be a positive detection of the flame of interest. When no light matches the parameters, it may be assumed that the flame of interest is not being produced by the burner.

In this way, a malfunction at a particular burner can be identified. The flame detector then may output one or more control signals, depending on whether the flame was detected.

Proper use of a flame detector may depend on the ability of technicians to program the flame detector to detect a flame with desired parameters. However, programming a flame detector can often be complicated and difficult.

SUMMARY

According to one embodiment, a system includes a flame detector with a photon detecting portion and a processing portion, the processing portion including a processor-based device programmed to provide the following functions: receiving input regarding a type of burner and a type of fuel, applying a flame detection configuration to the burner scanner according to the received input, and performing a flame detection process according to the flame detection configuration.

According to another embodiment, a method for controlling a burner includes receiving input to indicate burner parameters including a burner type and a fuel type, based on the burner type and fuel type, applying a flame detection configuration to a flame detector device, and performing a flame detection process according to the flame detection configuration.

According to yet another embodiment, a computer program product having a computer readable medium tangibly recording computer program logic for programming and operating a flame detector, the computer program product includes code to receive input indicating a burner type and a fuel type, code to apply flame parameters to a flame detection algorithm, where the flame parameters are associated with the received input in a data structure, and code to discern whether a detected flame matches the flame parameters by the flame detection algorithm.

BRIEF DESCRIPTION OF THE DRAWINGS

FIG. 5 is an illustration of an example data structure, adapted according to one embodiment.

DETAILED DESCRIPTION

Figure 1:
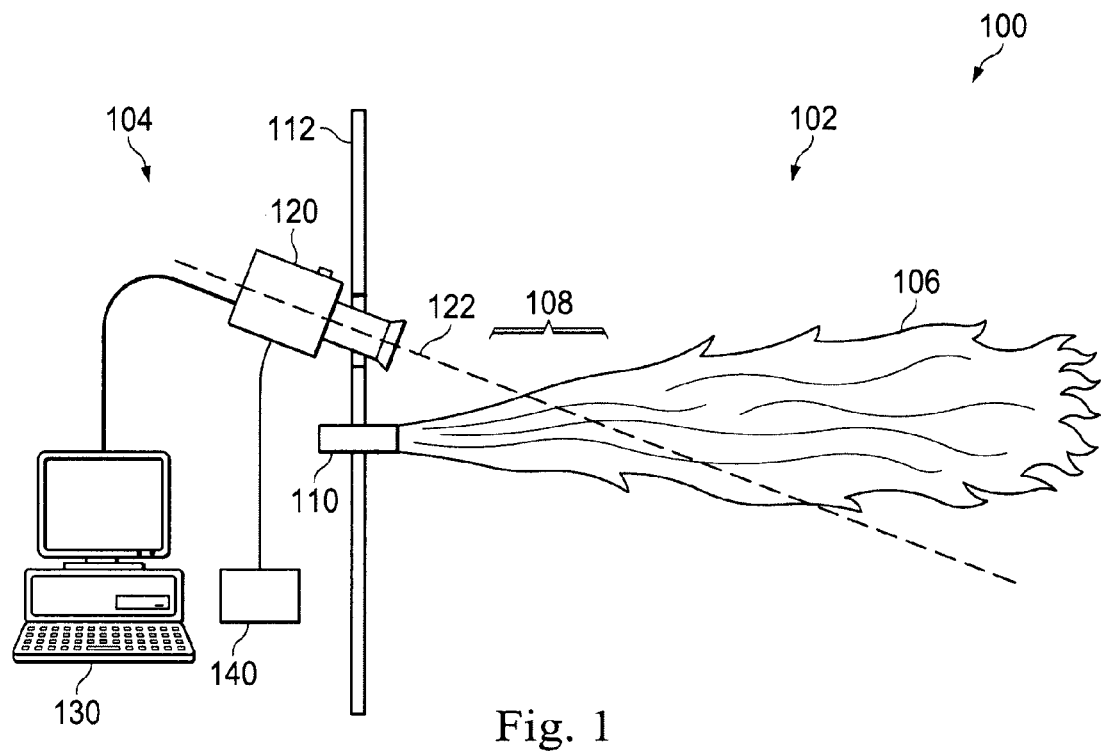
FIG. 1 is an illustration of an example application, adapted according to one embodiment.

It is to be understood that the following disclosure provides many different embodiments, or examples, for implementing different features of the present disclosure. Specific examples of components and arrangements are described below to simplify the present disclosure. These are, of course, merely examples and are not intended to be limiting.

Various embodiments include a flame detector that is simpler to program than conventional flame detectors. In one example, a flame detector has access to a data structure (e.g., a table or database) that has entries for a variety of different types of burners and a variety of different types of fuels. Each of the entries includes information for flame parameters, such as maximum intensity, minimum intensity, and frequency.

When a technician desires to program the flame detector he or she indicates a burner type and a fuel type. For instance, the technician may click on the configure button on Human Machine Interface (HMI) program or use a push button interface on the flame detector to select a burner type and a fuel type, where the selection of both pieces of information corresponds to a set of flame parameters in an entry within the data structure. Software and/or firmware in the flame detector use the flame parameters from the data structure entry to apply a configuration to the flame detector. Thus, in one example, a processor in the flame detector accesses the appropriate flame parameters and applies those parameters to a flame detection algorithm to identify flames that conform to those parameters.

Various embodiments assume that a particular burner model, when installed and used according to instructions with a particular fuel, creates an identifiable flame that should have consistent parameters among different applications. For instance, burner model A from Company Y when used with fuel Z should produce a flame with a particular profile in all or nearly all of the applications in which it may be used. Embodiments described herein take advantage of this characteristic of burners by employing a data structure with parameters from a variety of different burner model/fuel combinations. Thus, some examples include creating the data structure by examining flames produced by a multitude of different burner model/fuel combinations, recording the parameters of those flames, and entering those parameters into a data structure.

It was mentioned above that a particular flame may appear to have a different frequency (and max/min intensities) depending on which portion of the flame is observed. Generally, a burner flame is expected to have a higher frequency and min intensity closer to the burner nozzle. Thus, some embodiments assume that the various entries in the data structure have flame parameters for a particular observation position on a flame.

In some embodiments the data structure is saved to non-volatile memory within the flame detector, where a processor in the flame detector accesses the data structure to load flame parameters for use in the flame detection algorithm. However, other embodiments may provide access to the data structure in other manners. For instance, another embodiment may provide for a wired or wireless connection between a flame detector and a resource providing the data structure, such as a where a network-connected flame detector accesses the data structure over the network. Such embodiments may allow for updating the data structure to accommodate data from new flame detector model/fuel combinations.

FIG. 1 is an illustration of example application 100, adapted according to one embodiment. Application 100 includes a flame detector, according to the present disclosure, deployed to detect flame.

FIG. 1 illustrates space 102 inside of the combustion chamber of application 100, whereas space 104 is outside of the combustion chamber. Burner 110 produces flame 106 inside the combustion chamber, and flame detector 120 observes flame 106. While not explicitly shown in FIG. 1, it is understood that burner 110 receives a fuel (e.g., oil, coal, or natural gas) and combusts the fuel to produce flame 106.

In this example, the line of sight 122 of flame detector 120 is at an acute angle with respect to the burner 110, which is oriented perpendicularly to the wall 112 of the combustion chamber. This arrangement allows flame detector 120 to view flame 106 at viewing portion 108. As explained above, flame 106 should exhibit an identifiable max/min intensity and frequency when observed at viewing portion 108.

Furthermore, while not shown herein, the combustion chamber may include other burners, some of which may produce flames within line of sight 122. Flame detector 120 is configured with parameters corresponding to flame 106 at viewing portion 108 to allow flame detector 120 to differentiate between flame 106 and any other flames inside the combustion chamber.

Flame detector 120 is in communication with controller 130, which may include a laptop computer or other computer that interfaces with flame detector 120. Some embodiments use the controller 130 to send configuration parameters to flame detector 120, as explained in more detail below. Further, in some embodiments, flame detector 120 reports flame status back to controller 130, thereby allowing an operator of a power plant to watch the real time status of a burner (flame status). Additionally, in this example, Burner Management System (BMS) 140 receives a data signal from the flame detector 120 to indicate whether burner 110 is working properly. Thus, in one example, if flame detector 120 detects flame 106 as corresponding to the correct profile of flame parameters, then flame detector 120 may assert or de-assert a signal indicating such. Additionally or alternatively, flame detector 120 may assert or de-assert a signal to indicate that it does not detect a flame with the correct flame parameters. In any event, flame detector 120 reports the flame status to BMS 140. BMS 140 recognizes the assertion or de-assertion of the signal and may take appropriate action, such as cutting off a fuel (not shown) that supplies burner 110, in the event that the flame may be off. Any appropriate manner of asserting or de-asserting a signal for control purposes is within the scope of embodiments, and flame status may include any appropriate information, such as flame relay, flame intensity, system alarm, and the like.

Additionally, it should be noted that the application shown in FIG. 1 is for example only. The arrangement shown in FIG. 1, in which burner 110 is placed perpendicularly to wall 112, may be referred to as a tangential arrangement. Front fire arrangements (in which multiple rows of burners are used in a chamber), arch arrangements (in which burners are aligned in a downward angle and flames form a "V" shape) and any other arrangements of burners may use one or more flame detectors adapted according to the description herein.

Moreover, application 100 represents any type of burner application now known or later developed. For instance, the embodiments described herein may be applied to boilers, petrochemical refineries, incinerators, power generators, and the like.

Figure 2:
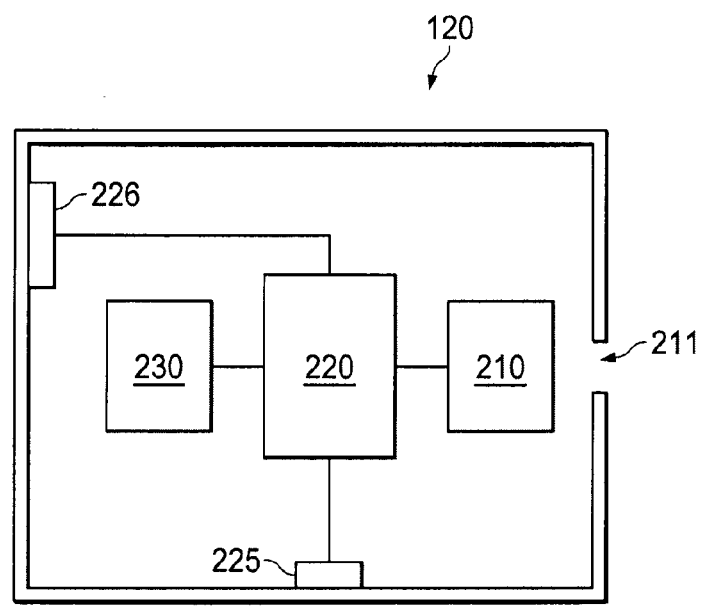
FIG. 2 is an illustration of an example embodiment of the flame detector of FIG. 1.

FIG. 2 is an illustration of an example embodiment of flame detector 120. FIG. 2 is a block diagram showing a conceptual representation of the hardware of one embodiment.

Flame detector 120 includes photon detector 210, which is in communication with processor 220. Processor 220 is in communication with memory 230, input/output port 225, and user interface device 226. It is understood, of course, that physical implementations of flame detector 120 may include many other features, such as mounting brackets, heat shielding and venting components, a ruggedized casing, and the like. It is also understood that various physical implementations may have a form factor that is especially adapted to use in industrial applications, whereas FIG. 2 shows flame detector 120 as a block for convenience of illustration. Any appropriate physical implementation is within the scope of embodiments.

Photon detector 210 receives light through aperture 211. When mounted as shown in FIG. 1, photon detector 210 receives light from flame 106 and generates electrical signals therefrom. One example implementation of a photon detector 210 includes a Charge Coupled Device (CCD), though the scope of embodiments may include any appropriate photon detecting device, such as a Complementary Metal Oxide Semiconductor (CMOS) active pixel sensor.

While a flame produces visible light, flames also produce light in other portions of the electromagnetic spectrum, such as infrared and ultraviolet light. Thus, flame detector 120 may employ a photon detector 210 that detects light in any appropriate part of the electromagnetic spectrum. In one example, photon detector 210 is adapted for sensing infrared light in the 800-1000 nm wavelength range. In another embodiment, photon detector 210 is adapted for sensing ultraviolet light (e.g., in 300-350 nm range) and/or visible light (in a range between ultraviolet and infrared). Other embodiments may include more than one photon detector to sense multiple types of light.

Processor 220 may include any appropriate type of processor, such as a general purpose processor, an Application Specific Integrated Circuit (ASIC), a Digital Signal Processor (DSP), and/or the like. Processor 220 executes computer-readable code to provide flame detection functionality. For instance, processor 220 receives electrical signals from photon detector 210, the electrical signals being indicative of the light received from a flame. Processor 220 then compares information represented by the electrical signals to a flame profile to thereby discern whether a currently viewed flame matches the profile.

Processor 220 is also in communication with input/output port 225. In some embodiments, input output port 225 may be adapted to couple to an 8-wire cable (not shown), which communicates data between a controller (e.g., 130 of FIG. 1) and processor 220. In some instances, a cable at port 225 may also provide power.

As mentioned above, flame detector 120 may assert or de-assert a signal depending on whether it detects a flame matching a profile of interest. Such signal may be provided at port 225 by processor 220. Other embodiments may include additional ports or may communicate data using wireless protocols. In fact, any appropriate communication technique, whether wired or wireless is within the scope of embodiments.

Processor 220 is also in communication with user interface device 226. Any appropriate hardware features may be included in user interface device 226. Examples include a keypad, a display screen, indicator lights, and the like. A human user may use interface device 226 to enter information, such as a burner type and a fuel type. In some instances, flame detector 120 may be programmed using an external device, such as a laptop computer, in which case a user may interface with the other device rather than directly with hardware at flame detector 120. The scope of embodiments is not limited to any particular interface device nor to any technique for a user to enter information to program flame detector 120.

Flame detector 120 also includes memory 230, which in this example is used to store the data structure discussed above. Memory 230 may include any appropriate type of memory, such as flash memory, EEPROM, a hard disk, and/or the like. Memory 230 may be pre-programmed before being distributed to an end user and/or may be programmed or updated in any appropriate manner. Processor 220 accesses memory 230 to retrieve one or more entries from the data structure, where processor 220 uses an accessed entry to configure itself to detect a flame. While memory 230 is shown as being separate from processor 220, other embodiments may integrate memory 230 into a chipset embodying processor 220.

When implemented via computer-executable instructions, various elements of embodiments of the present disclosure are in essence the software code defining the operations of such various elements. The executable instructions or software code may be obtained from a tangible readable medium (e.g., a hard drive media, optical media, RAM, EPROM, EEPROM, tape media, cartridge media, flash memory, ROM, memory stick, network storage device, and/or the like). In fact, readable media can include any medium that can store information. In this example, memory 230 may serve as storage for the computer-readable instructions that allow processor 220 to perform flame detection algorithms. Other embodiments may use a different memory (not shown) that is either integrated or not integrated with processor 220 as appropriate. For instance, one embodiment may employ an ASIC with hardware pre-programmed to include instructions providing flame detection functionality.

In accordance with embodiments of the present disclosure, processor 220 performs specific operations by executing one or more sequences of one or more instructions contained in system memory. Such instructions may be read into system memory from another computer readable medium (not shown).

Figure 3:
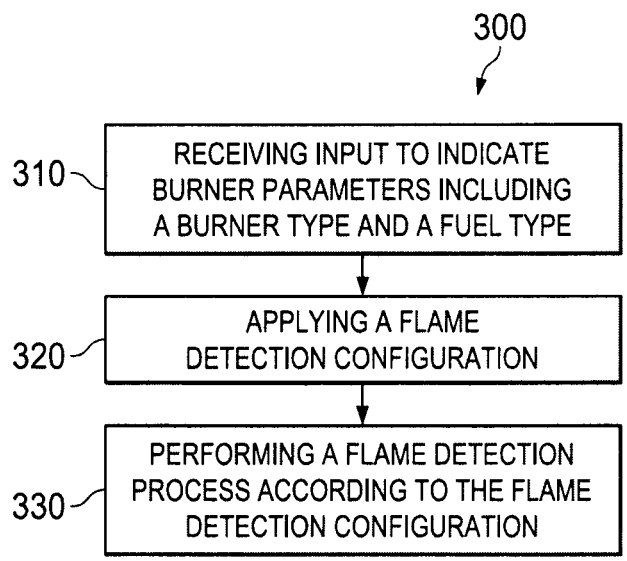
FIG. 3 is an illustration of an example method, adapted according to one embodiment.

FIG. 3 is an illustration of example method 300, adapted according to one embodiment. Method 300 may be performed by processor 220 as it executes code to provide flame detection functionality.

At action 310, the processor receives input to indicate burner parameters including a burner type and a fuel type. In one example, a human user enters information using a user interface device associated with the flame detector. For instance, the user interface device may include one or more keys that allow a user to browse a list of burner types and enter a selected a burner type and then browse a list of fuels and enter a fuel type. Further in this example, the user interface device may include a display (such as a Liquid Crystal Display, LCD) to provide visual feedback to the user, such as by rendering a name of a burner type and/or fuel type, as the user browses and selects.

In another example, the data is received from an external device that communicates either wired or wirelessly with the processor. Any appropriate manner of entering the information may be adapted for use in one or more embodiments.

As discussed above, embodiments described herein may be advantageous when compared to conventional flame detectors. Specifically, embodiments that access flame parameters through use of burner/fuel type input may be more easily programmed by a technician than are some conventional flame detectors. In other words, a technician is generally expected to know the burner model and fuel type for a given burner, and entering such information should simply be a matter of operating a user interface and entering such information. In some embodiments, the technician is not expected to know the flame parameters themselves (max/min intensity and frequency) nor to program the flame detector by recording parameters from the flame itself. Nevertheless, various embodiments do not exclude the possibility of a technician entering additional configuration and programming information, as appropriate.

At action 320, the processor applies a flame detection configuration. In one example, the burner/fuel type data received at action 310 corresponds to an entry in a data structure, where the entry includes flame parameters that are associated with a burner/fuel type combination. The various parameters may include minimum and maximum intensity and frequency, as mentioned above. Any additional useful parameters may also be included in the data structure.

As one example, the flicker frequency of a flame in a burner application is generally in the range of 3 Hz to 130 Hz, which is affected by area of the flame being viewed and pulsation of fuel. In many instances, the flicker of the flame may not be perceptible to a human observer. Intensity of the flame can be measured in power per unit area, and it will be affected by viewing portion of the flame. Rather than directly measure minimum and maximum intensity, some embodiments may instead measure an intensity amplitude difference during the flame's cycle.

Applying the configuration in this example includes using one or more flame parameters in the flame detection algorithm.

At action 330, the processor performs a flame detection algorithm. A flame detection algorithm, explained in more detail with respect to FIG. 4, attempts to discern whether a flame with the given parameters is observed. Any method of matching a flame to a flame profile is within the scope of embodiments.

Method 300 is offered as an example, and it is understood that various embodiments may add, omit, rearrange, or modify one or more actions. For instance, the flame detection algorithm of action 330 may include a loop that is repeated and/or continually performed. Furthermore, additional actions, such as displaying errors or warning of device malfunctions may be performed as well.

Figure 4:
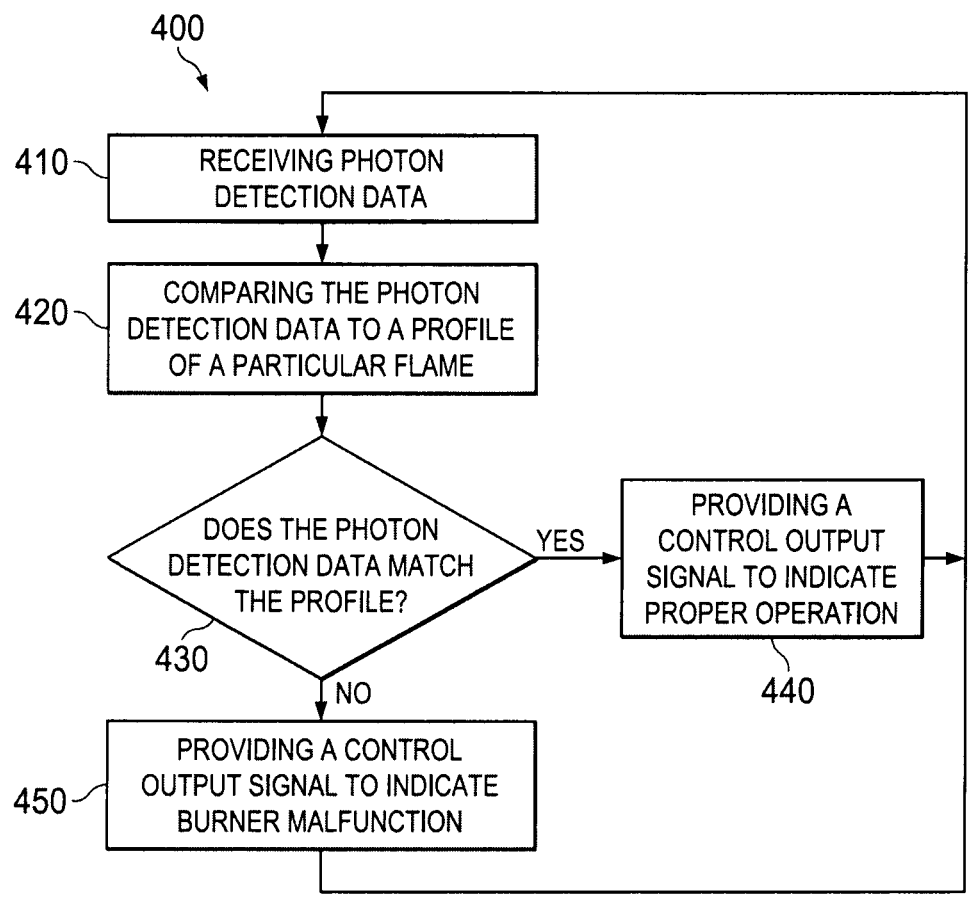
FIG. 4 is an illustration of an example flame detection algorithm according to one embodiment.

FIG. 4 is an illustration of an example flame detection algorithm 400 according to one embodiment. Method 400 may be performed by processor 220 (FIG. 2) as it executes code to provide flame detection functionality.

At action 410, the processor receives photon detection data. For instance, as the photon detection device 210 (FIG. 2) receives photons within a particular spectrum, it may output electrical signals that are indicative of the photons it detects. Processor 220 receives the data and interprets the data, as shown below in the processing at actions 420, 430.

At action 420, the processor compares the photon detection data to a profile of a particular flame. For instance, it was described with respect to FIG. 3 how the processor may access a data structure to acquire information regarding a flame profile. The flame profile may include parameters such as max/min intensity and frequency.

In one embodiment, the processor may make a simple comparison of the parameters in the profile to the photon detection data. For instance, the processor may derive max/min intensity information and frequency information from the photon detection data, process the derived information and then compare the results from the derived information to the flame profile to within an acceptable tolerance. However, other embodiments may include more sophisticated statistical analysis of the received photon data and the flame profile to produce more reliable comparisons. For instance, the photon detection data may include data from flames other than the particular flame of interest, and the algorithm may include analysis to differentiate the flame of interest from other flames within the line of sight. Any technique to identify a flame using flame parameters is within the scope of embodiments.

Action 430 is a decision wherein the processor uses logic to discern whether the photon detection data matches the profile. If the photon detection data is a match, then method 400 branches to action 440, wherein the processor provides a control output signal to indicate proper operation. In one example, a high signal (e.g., 5V) is indicative of proper operation, and the processor provides a high signal. In another example, a low signal (e.g., 0V) is indicative of proper operation. In any event, assertion or de-assertion of a signal satisfies action 440. In yet another example, flame detector 120 communicates via a network and may send a packet identifying proper operation.

If the photon detection data is not a match, then method 400 branches to action 450, where the processor provides a signal to indicate a burner malfunction. In examples including high and low signals, asserting a de-asserting the signal in a manner opposite that used to indicate proper operation may satisfy action 450. In yet another example, flame detector 120 communicates via a network and may send a packet identifying proper operation.

Method 400 is offered as an example, and it is understood that various embodiments may add, omit, rearrange, or modify one or more actions. For instance, method 400 may be repeated and/or continually performed, thereby forming a loop as shown by actions 440 and 450 looping back to action 410. Furthermore, additional actions, such as displaying errors or warning of device malfunctions may be performed as well.

FIG. 5 is an illustration of example data structure 500, adapted according to one embodiment. The embodiments described herein may use any appropriate data structure, such as a table, a file, a database, and the like, though FIG. 5 illustrates a table.

In the example of FIG. 5, data structure 500 has dimension 520, providing a multitude of columns, each devoted to a type of fuel. Examples of fuel types include oil, coal, and gas, though any fuel type may be represented in some instances. Dimension 510 provides a multitude of rows, each of the rows devoted to a particular burner type. Examples of burner types include a manufacturer/model combination. Embodiments described herein may accommodate entries for any appropriate number of burner types and fuel types.

Each cell in the table, such as cell 530, is at an intersection of a row and a column and provides data indicating flame parameters for a given burner type and fuel type. The processor may access flame parameters by being directed to a particular cell or by traversing the structure for a particular cell using burner type/fuel type information.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the disclosure, even though not specifically shown in the drawings or described in the text.

The invention claimed is:

1. A system comprising:
a flame detector with a photon detecting portion and a processing portion, the processing portion including a processor-based device programmed to provide the following functions:
during programming receiving input indicating a type of burner and a type of fuel;
looking up a flame detection configuration in a data structure based on the received input indicating the type of burner and the type of fuel, the data structure comprising pre-stored entries representing flame parameters for combinations of burner types and fuel types, each one of the pre-stored entries comprising a unique set of flame parameters based on a respective match between a burner type and a fuel type;
applying the flame detection configuration to the burner scanner, the flame detection configuration comprising flame parameters associated with a match of both the type of burner and the type of fuel indicated by the received input; and
performing a flame detection process according to the flame detection configuration.

2. The system of claim 1 in which the flame detection configuration includes the following flame parameters; an indication of an intensity of a flame and frequency of flame flicker.

3. The system of claim 1 in which applying the flame detection configuration comprises:
setting an operation of the flame detector to examine photon detection data to identify a particular flame at a particular flicker frequency.

4. The system of claim 1 in which the flame detection process comprises:
receiving photon detection data;

processing the photon detection data and identifying the processed photon detection data with a profile, the profile comprising the flame parameters corresponding to the entry; and providing a control output signal to indicate proper operation if the photon detection data corresponds to a range of the flame parameters.

5. The system of claim 1 in which the flame detection process comprises:
differentiating a particular flame from photon detection data of a plurality of flames.

6. The system of claim 1 in which input regarding a type of burner comprises:
input indicating a burner model.

7. The system of claim 1 in which input indicating a type of fuel comprises:
input indicating one or more of oil, natural gas, or coal.

8. The system of claim 1 in which the photon detecting portion detects one or more of Ultraviolet light, infrared light, and visible light.

9. A method for controlling a burner comprising:
receiving input to select a known burner type and a known fuel type;
looking up a flame detection configuration in a data structure based on the received input, the data structure comprising pre-stored entries representing flame parameters for combinations of burner types and fuel types, each one of the pre-stored entries comprising a unique set of flame parameters based on a respective match between a burner type and a fuel type;
based on an entry within the data structure corresponding to the known burner type and known fuel type, applying a flame detection configuration to a flame detector device, the flame detection configuration being specific to a match of the known burner type and the known fuel type; and
performing a flame detection process according to the flame detection configuration.

10. The method of claim 9 further comprising:
based on the flame detection process, outputting a signal indicating a burner malfunction to a burner controller; and
modifying operation of the burner by the burner controller in response to the signal.

11. The method of claim 9 in which the flame detection configuration includes the following flame parameters: a maximum flame intensity, a minimum flame intensity, and flame flicker frequency.

12. The method of claim 9 in which the flame detection process comprises:
receiving photon detection data;
processing the photon detection data and identifying the processed photon detection data with the flame parameters corresponding to the entry; and
providing a control output signal to indicate proper operation.

13. The method of claim 9 in which applying a flame detection configuration comprises:
accessing flame parameters associated with the burner type and the fuel type; and
using the flame parameters in the flame detection algorithm.

14. A computer program product having a computer readable medium tangibly recording computer program logic for programming and operating a flame detector, the computer program product comprising:
code to receive input indicating a burner type and a fuel type during programming;
code to look up a flame detection configuration in a data structure based on the received input, the data structure comprising pre-stored entries representing flame parameters for combinations of burner types and fuel types, each one of the pre-stored entries comprising a unique set of flame parameters based on a respective match between a burner type and a fuel type;
code to apply flame parameters to a flame detection algorithm, where the flame parameters are associated with the entry corresponding to the received input; and
code to discern whether a detected flame corresponds to a range of the flame parameters by the flame detection algorithm.

15. The computer program product of claim 14 further comprising:
code to output a signal, in response to discerning whether the detected flame matches the flame parameters, indicating a burner malfunction to a burner controller.

16. The computer program product of claim 14 in which the flame parameters comprise a maximum flame intensity, a minimum flame intensity, and flame flicker frequency.

17. The computer program product of claim 14, in which the code to discern comprises:
code to receive photon detection data;
code to compare the photon detection data to the flame parameters of the entry corresponding to the received input; and
code to provide a control output signal in response to checking for proper operation.

18. The computer program product of claim 14, further comprising:
code to navigate the data structure by burner type and fuel type.

19. The computer program product of claim 14, in which the code to discern comprises:
code to identify the detected flame from among other flames in a line of sight of the flame detector.

20. The method of claim 9 wherein the burner type comprises a burner model.

* * * * *